(12) United States Patent
Nankawa et al.

(10) Patent No.: US 11,406,929 B2
(45) Date of Patent: Aug. 9, 2022

(54) COMPOUND, SYNTHESIS METHOD THEREOF, AND SEPARATION AND RECOVERY AGENT THEREOF

(71) Applicant: Japan Atomic Energy Agency, Ibaraki (JP)

(72) Inventors: Takuya Nankawa, Tokai (JP); Matthew Rosseinsky, Liverpool (GB); David Stewart, Liverpool (GB); Alexandros Katsoulidis, Liverpool (GB)

(73) Assignee: Japan Atomic Energy Agency, Ibaraki (JP)

( * ) Notice: Subject to any disclaimer, the term of this patent is extended or adjusted under 35 U.S.C. 154(b) by 12 days.

(21) Appl. No.: 15/680,397

(22) Filed: Aug. 18, 2017

(65) Prior Publication Data

US 2018/0050920 A1    Feb. 22, 2018

(30) Foreign Application Priority Data

Aug. 19, 2016    (JP) .............................. JP2016-161059

(51) Int. Cl.
*B01D 53/00*        (2006.01)
*B01D 53/02*        (2006.01)
*C07C 55/07*        (2006.01)
*G21F 9/12*         (2006.01)
*B01J 20/22*        (2006.01)
*C01F 17/271*       (2020.01)
*C07C 69/36*        (2006.01)

(52) U.S. Cl.
CPC ............ *B01D 53/02* (2013.01); *B01D 53/00* (2013.01); *B01J 20/226* (2013.01); *C01F 17/271* (2020.01); *C07C 55/07* (2013.01); *C07C 69/36* (2013.01); *G21F 9/12* (2013.01); *B01D 2253/116* (2013.01); *B01D 2257/93* (2013.01)

(58) Field of Classification Search
CPC .................................................. C01F 17/0043
USPC .......................................................... 436/56
See application file for complete search history.

(56) References Cited

FOREIGN PATENT DOCUMENTS

JP    2016-70781 A    5/2016
JP    2016-80486 A    5/2016

OTHER PUBLICATIONS

J.-C. Trombe et al. "Synthesis, crystal structure of Gd(H2O)(C2O4)2 • NH4 and of La(C2O4)2 • NH4. Characterization of the Ln(H2O)(C2O4)2 • NH4 with Ln=Eu . . . Yb" Solid State Sciences 3 (2001) 309-319 (Year: 2001).*
Eva Hansson "Structural Studies on the Rare Earth Carhoxylates: 5. The Crystal and Molecular Structure of Neodymium(III) Oxalate 10.5—Hydrate" Acta Chemica Scandinavica (1970), 24(8), 2969-82 (Year: 1970).*

* cited by examiner

*Primary Examiner* — Christine T Mui
*Assistant Examiner* — Emily R. Berkeley
(74) *Attorney, Agent, or Firm* — Crowell & Moring LLP (57) ABSTRACT

To provide a new compound with pores finely tunable in size so as to take up a specific element and release the specific element taken up in the pores as necessary, a synthesis method of the new compound, and a separation and recovery agent. The new compound represented by the following molecular formula:

$(NH_4)[Ln(C_2O_4)_2(H_2O)]$ wherein Ln represents a lanthanide selected from Sm, Eu, Tb, Dy, Ho, Er, Tm, Yb, and Lu.

1 Claim, 6 Drawing Sheets

| CRYSTALLOGRAPHIC PARAMETERS | |
|---|---|
| COMPOUNDS | $(NH_4)[Tb(C_2O_4)_2(H_2O)]$ |
| FORMULA | $C_4H_6NO_9Tb$ |
| CRYSTAL SYSTEM | MONOCLINIC |
| SPACE GROUP | P2/n |
| a (Å) | 9.380(5) |
| b (Å) | 6.130(4) |
| c (Å) | 7.851(5) |
| β (°) | |
| V (Å³) | 451.4 |
| Z | 2 |
| $R(F_0)/R_W(F_0)$ | 0.0380/0.0746 |

STRUCTURE OF $(NH_4)[Tb(C_2O_4)_2(H_2O)]$

STRUCTURE OF $(NH_4)[Tb(C_2O_4)_2(H_2O)]$

FIG. 4B

| CRYSTALLOGRAPHIC PARAMETERS | |
|---|---|
| COMPOUNDS | $(NH_4)[Tb(C_2O_4)_2(H_2O)]$ |
| FORMULA | $C_4H_6NO_9Tb$ |
| CRYSTAL SYSTEM | MONOCLINIC |
| SPACE GROUP | $P2/n$ |
| $a$ (Å) | 9.380(5) |
| $b$ (Å) | 6.130(4) |
| $c$ (Å) | 7.851(5) |
| $\beta$ (°) | |
| $V$ (Å$^3$) | 451.4 |
| $Z$ | 2 |
| $R(F_0)/R_W(F_0)$ | 0.0380/0.0746 |

| ADSORBENTS | IONS | INITIAL CONCENTRATION ppm | $K_d$ cm$^3$/g | REFERENCES |
|---|---|---|---|---|
| (NH4)[Tb(C2O4)2(H2O)] | $Sr^{2+}$ | 182 | $3.1 \times 10^4$ | this work |
| (NH4)[Tb(C2O4)2(H2O)] | $Ba^{2+}$ | 200 | $1.4 \times 10^5$ | this work |
| Clinoptilolite | $Sr^{2+}$ | 100 | $3.3 \times 10^5$ | [1] |
| Mordenite | $Sr^{2+}$ | 100 | $2.4 \times 10^5$ | [1] |
| Zeolite A | $Sr^{2+}$ | 100 | $5.1 \times 10^5$ | [1] |
| Zeolite X | $Sr^{2+}$ | 100 | $6.1 \times 10^5$ | [1] |

[1] Database of Promising Adsorbents for Decontamination of Radioactive Substances, http://reads.nims.go.jp/index_en.html

| component | concentration | |
|---|---|---|
| NaCl | 22.1 | g/l |
| MgCl$_2$ · 6H$_2$O | 9.9 | g/l |
| CaCl$_2$ · 2H$_2$O | 1.5 | g/l |
| Na$_2$SO$_4$ | 3.9 | g/l |
| KCl | 0.61 | g/l |
| NaHCO$_3$ | 0.19 | g/l |
| KBr | 96 | mg/l |
| Na$_2$B$_4$O$_7$·10H$_2$O | 78 | mg/l |
| SrCl$_2$ | 13 | mg/l |
| NaF | 3 | mg/l |
| LiCl | 1 | mg/l |
| KI | 81 | µg/l |
| MnCl$_2$ · 4H$_2$O | 0.6 | µg/l |
| CoCl$_2$ · 4H$_2$O | 2 | µg/l |
| AlCl$_2$ · 4H$_2$O | 8 | µg/l |
| FeCl$_3$ · 6H$_2$O | 5 | µg/l |
| Na$_2$WO$_4$· 2H$_2$O | 2 | µg/l |
| (NH$_4$)$_6$Mo$_7$O$_{24}$· 4H$_2$O | 18 | µg/l |

COMPOUND, SYNTHESIS METHOD THEREOF, AND SEPARATION AND RECOVERY AGENT THEREOF

BACKGROUND OF THE INVENTION

Technical Field

The present invention relates to a new compound, a method for synthesizing the new compound, and an element separating and recovering agent. The new compound is made up of a coordination polymer that contains highly-ordered pores whose size is finely tunable.

Background Art

Radioactive elements, such as strontium and cesium, are known to be typically separable by materials with pores, such as zeolites and Prussian blue, as is disclosed in JP 2016-80486 A and JP 2016-70781 A. Also, in general, water contaminated with radioactive materials, namely radioactive waste solutions, is subjected to a treatment process in which, for example, the radioactive elements are adsorbed by granular zeolites to lower the contamination level before being released to the sea or the like.

REFERENCES

[Patent Literature 1] JP 2016-80486 A
[Patent Literature 2] JP 2016-70781 A

BRIEF SUMMARY OF THE INVENTION

Technical Problem

Unfortunately, however, it is very difficult for microporous materials such as zeolites and Prussian blue to efficiently separate and recover only a specific element from waste solutions (radioactive waste solutions, general industrial effluents, etc.) due to their extremely rigid structures and constant pore sizes. In addition, it is particularly difficult to take out the elements separated from waste solutions from such microporous materials, which prevents recycling of the separated elements.

And there is another problem. Take zeolites, for example, which have been conventionally used for this purpose. Used zeolites, which have taken up cesium, are radioactive wastes themselves, resulting in an increased amount of radioactive wastes.

In view of the above problems in the conventional art, the present invention has an object to provide a new compound with pores finely tunable in size so as to take up a specific element and release the specific element taken up in the pores as necessary, a method for synthesizing the new compound, and an element separating and recovering agent.

Solution to Problem

According to an aspect of the present invention, a new compound is represented by the following formula:

$(NH_4)[Ln(C_2O_4)_2(H_2O)]$ wherein Ln is Sm, Eu, Tb, Dy, Ho, Er, Tm, Yb, or Lu.
By appropriately selecting the lanthanide metal (Ln), the amount of lanthanide contraction can be easily controlled. As a result, the new compound above is capable of efficiently separating and recovering a specific element from waste solutions as described above, for example. Therefore, the new compound finds an application as an element separating and recovering agent for separating and recovering a specific element.

(1) Specifically, the element separating and recovering agent to be used for the above purpose is made up of a coordination polymer. The coordination polymer has a structure with pores that are finely tunable in size by 0.1 Å or smaller through selection of the ions to be used for synthesis of the coordination polymer. Such a fine pore size tuning has never been possible with conventional materials. This fine pore size tuning makes it possible to change the pore size according to a specific purpose, namely to separate specific metal ions from a particular environment. Therefore, it is possible to obtain an ion separation agent that is best suited to a specific situation, for example, where small ions need to be removed from relatively large ions. As a result, it is now possible to separate strontium from seawater, which would be quite difficult with ordinary zeolites, for example, by tuning the pore size of this coordination polymer to meet the specific purpose.

(2) Since the coordination polymer has a structure that is more flexible in responding to the change of a solution than those of zeolites and Prussian blue, it is capable of releasing the ions it has taken up under an acidic condition at a pH value of around 4. This property makes it possible not only to separate a specific element into the element separating and recovering agent as effectively as conventional materials such as zeolites and Prussian blue, but also to recover the element. Isolation and recovery of radioactive cesium or strontium utilizing this method would open up the possibilities for use of radioisotopes as radiation sources and heat sources. Also, the used coordination polymer can be restored to its original state by subjecting it to a synthesis reaction, which means that waste is not produced, unlike the case with zeolites having adsorbed radioactive elements. Since this element separating and recovering agent is capable of separating and recovering radioactive elements from waste solutions or the like, it does not increase the amount of radioactive waste in large quantity, which is another advantage.

Also, according to another aspect of the present invention, the new compound described above is synthesized by a reaction expressed by the following formula:

[Formula 1]

wherein Ln is Sm, Eu, Tb, Dy, Ho, Er, Tm, Yb, or Lu.

Advantageous Effects of Invention

Since its pores can be finely tuned in size to take up a specific element, with the new compound according to an embodiment of the present invention, when it is used as an element separating and recovering agent, separation of strontium from seawater, which is difficult with ordinary zeolites, is made possible by tuning the pore size of the coordination polymer that configures this element separating and recovering agent to meet the specific purpose.

Also, since it is capable of releasing as necessary the specific element that it has taken up into its pores, with the new compound according to an embodiment of the present invention, separation and isolation of radioactive cesium or strontium, for example, is made possible by using it as an element separating and recovering agent. Moreover, the used coordination polymer, namely element separating and recovering agent, can be restored to its original state by subjecting it to a synthesis reaction. This means that it does not produce extra waste, such as zeolites having adsorbed radioactive elements, or increase the amount of radioactive waste in large quantity.

DETAILED DESCRIPTION OF THE PREFERRED EMBODIMENTS

First, a method for synthesizing a new compound that can be used as an element separating and recovering agent will be described referring to FIGS. 1 and 2. The new compound according to an embodiment of the present invention as described above was synthesized by a reaction expressed by the following formula:

[0017]

[Formula 2]

wherein Ln is Sm(samarium), Eu(europium), Tb(terbium), Dy(dysprosium),

Ho(holmium), Er (erbium), Tm(thulium), Yb(ytterbium), or Lu(lutetium).

As shown in Formula 2 above, the new compound according to an embodiment of the present invention was obtained by first immersing dimethyl oxalate and terbium chloride hexahydrate in an ammonium chloride-containing aqueous solution. The solution was then subjected to heating at 130° C. for 24 hours and filtering to separate colorless block-like crystals, which were cleansed.

Figure 1:
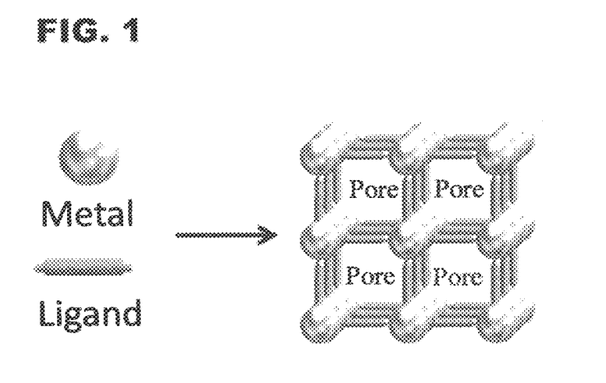
FIG. 1 is a schematic diagram illustrating the relationship between metal ions and ligands in a coordination polymer.

FIG. 1 is a schematic diagram illustrating the relationship between metal ions and ligands in the new compound, namely a coordination polymer, according to an embodiment of the present invention. The coordination polymer is synthesized by self-assembly of ligands and metal ions as shown in FIG. 1. In this self-assembly, portions that look like the interstices of a jungle gym are formed to become pores. Since a typical coordination polymer is obtained as a single crystal, the pores formed are highly ordered in size. Also, as suggested by FIG. 1, the pores of the coordination polymer are tunable in size by the ligand size and the metal ionic size. Normally, the pore size is tuned by changing the length of the ligands by several angstroms. In the present invention, however, the pore size is more finely tunable by changing the size of the metal ions finely.

Figure 2:
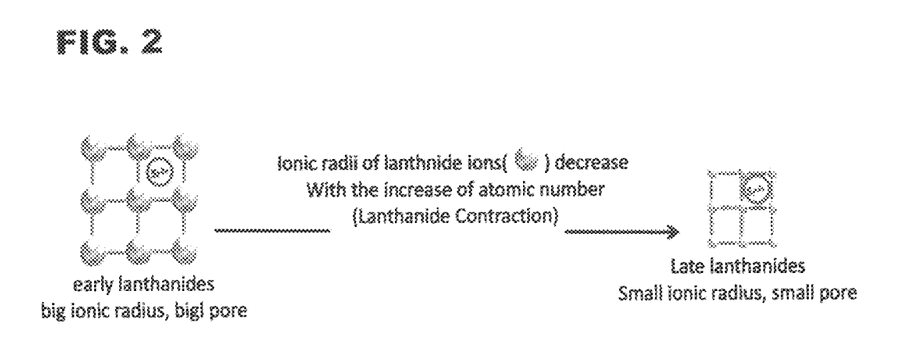
FIG. 2 is a schematic diagram illustrating lanthanide contraction.

FIG. 2 is a schematic diagram illustrating lanthanide contraction. The lanthanide ions that configure the coordination polymer synthesized according to an embodiment of the present invention, Sm, Eu, Tb, Dy, Ho, Er, Tm, Yb, and Lu, are known to reduce in radius as the atomic number becomes larger by a phenomenon called "lanthanide contraction" as schematically illustrated in FIG. 2. This means that metals with a relatively small atomic number such as Sm and Eu have relatively large pores, while elements with a relatively large atomic number such as Yb and Lu have relatively small pores. Normally, the variation in ionic radius among the 10 metal elements from Sm to Lu ranges from 0.2 Å to 0.3 Å. This fine variation allows fine pore size tuning.

Next, how to recover a specific metal selectively by using the synthesized new compound as an element separating and recovering agent will be described referring to FIG. 3.

Figure 3:
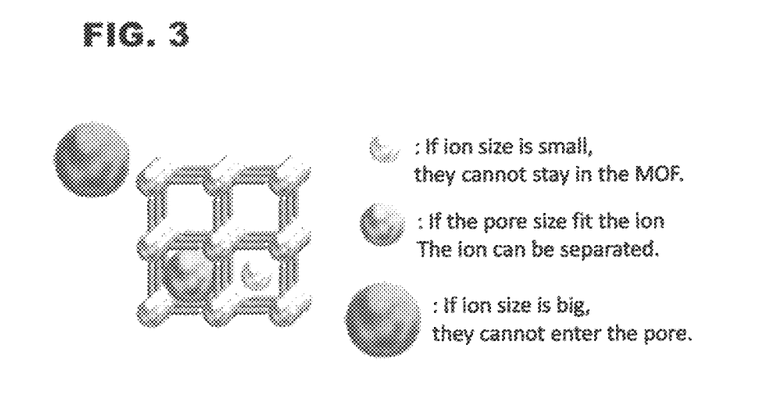
FIG. 3 is a schematic diagram illustrating the relationship between pore size and ionic size.

FIG. 3 is a schematic diagram illustrating the principle why conventional microporous materials such as zeolites and Prussian blue are capable of separating cesium and strontium. As understood from FIG. 3, ions that can be separated with conventional microporous materials are limited to those with an ionic size that matches the pore size of conventional microporous materials such as zeolites and Prussian blue. Metals with an ionic size smaller than the pore size as shown at the lower right of the figure cannot be separated, while metals with an ionic size larger than the pore size as shown at the upper left of the figure cannot be separated either.

In other words, only the ions with a size that matches the size of the pore size can be separated. Actually, the difference in radius size among elements is extremely minute, so it would be difficult to recognize only specific metal ions by changing the pore size by 0.1 Å or larger. In the present invention, in order to recognize this minute difference in ionic radius, the pore size of the coordination polymer can be finely tuned by 0.1 Å or smaller by using lanthanide ions, which exhibit slight variation in ionic radius, as a component of the coordination polymer, to separate only specific ions.

As an exemplary result, separation of strontium from seawater, which would be difficult with conventional zeolites, is made possible by tuning the pore size of this coordination polymer to meet the specific purpose. Also, based on this finding, it is now possible to select an ion separation agent that is best suited to a specific situation, for example, where small ions need to be removed from relatively large ions.

Next, how to separate the recovered metal from the element separating and recovering agent will be described. By the scheme described below, the element is separated in a neutral state and then placed under an acidic condition to be separated and recovered from the coordination polymer. The coordination polymer itself becomes $Ln_2(C_2O_4)_3$, to which ligands and ammonium salt is added so that it is restored to the original coordination polymer, namely $(NH_4)[Ln(C_2O_4)_2(H_2O)]$, by a synthesis reaction. Through the series of treatments as described above, the original coordination polymer can be regenerated while separating and recovering the element.

[Formula 3]

Figure 4A:
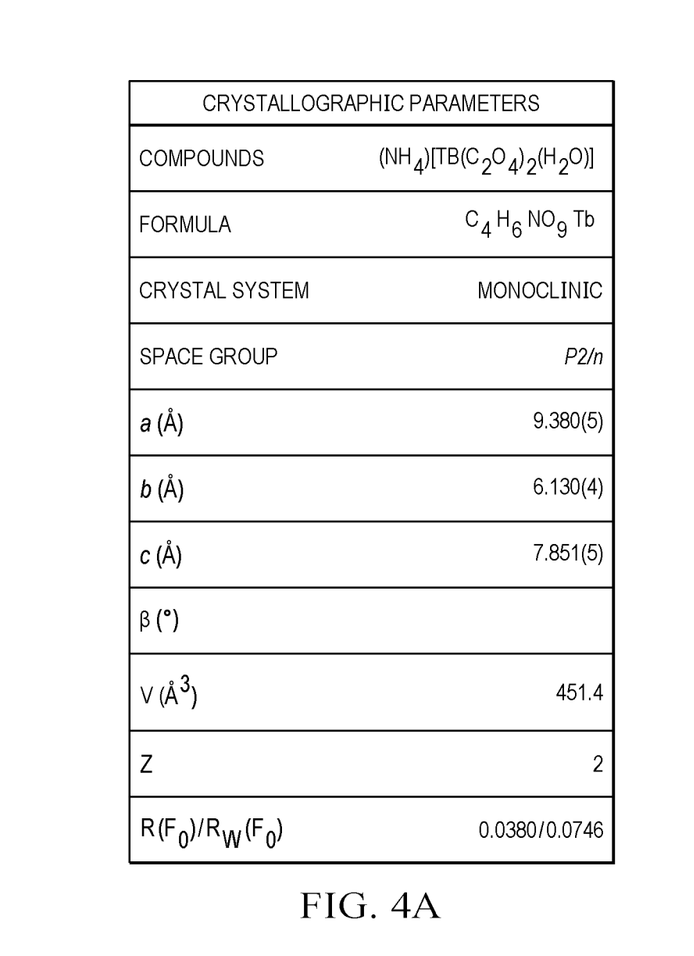
FIGS. 4A and 4B are a table and a diagram, respectively, showing results of single crystal X-ray structure analysis to illustrate the structure of an element separating and recovering agent according to an embodiment of the present invention.
Figure 4B:
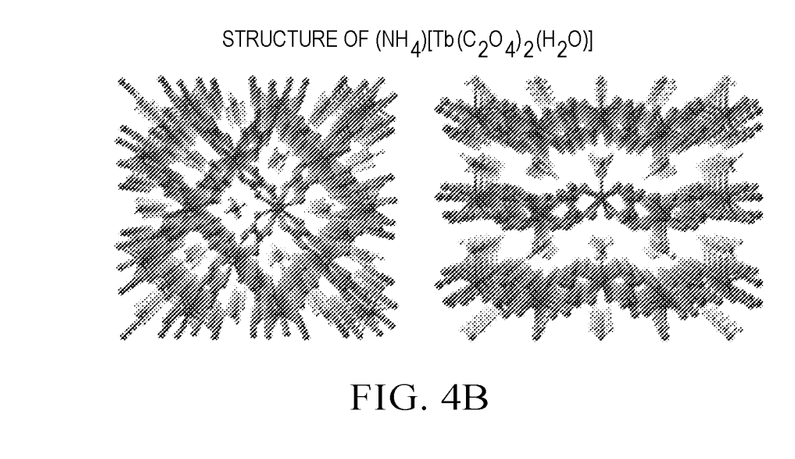

<Experiment 1> Synthesis of Element Separating and Recovering Agent $(NH_4)[Tb(C_2O_4)_2(H_2O)]$ FIGS. 4 (A) and 4 (B) show results of single crystal X-ray structure analysis to illustrate the structure of an element separating and recovering agent according to an embodiment of the present invention. FIG. 4 (A) is a table showing crystallographic parameters, and FIG. 4 (B) is a structural diagram.

The element separating and recovering agent $(NH_4)[Tb(C_2O_4)_2(H_2O)]$ as shown in FIGS. 4 (A) and 4 (B) was synthesized as follows. First, 3.0 g of dimethyl oxalate, 3.0 g of terbium chloride hexahydrate, 6.0 g of ammonium chloride, and 50 ml of water were heated at 130° C. for 24 hours. The solution was then subjected to filtering to separate colorless block-like crystals. The obtained crystals were cleansed with water (5 ml×3), ethanol (5 ml×3), and acetone (5 ml×3) and dried to obtain the element separating and recovering agent [yield: 2.58 g, percentage yield: 87% (in terms of terbium), elemental analysis: $C_4H_6NO_9Tb$: C, 12.95 (12.78); H, 1.63 (1.70); N, 3.78 (3.52)].

<Experiment 2> Uptake of Strontium and Barium in Pure Water

Figure 5:
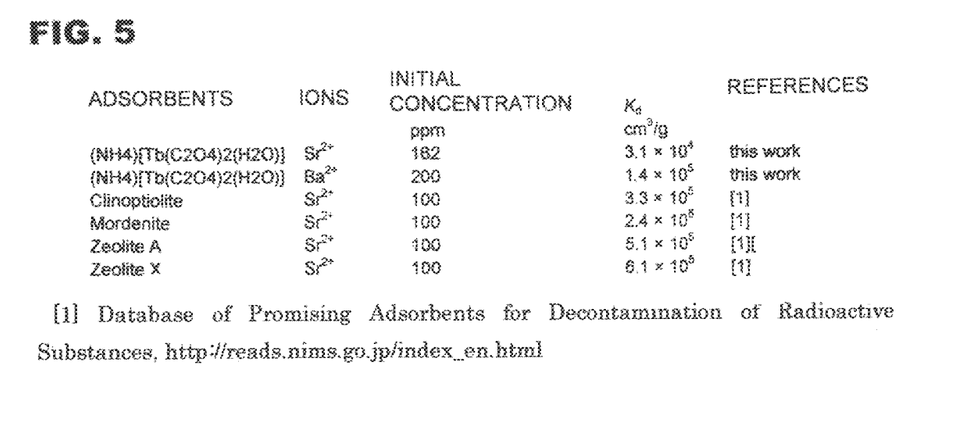
FIG. 5 shows comparison of distribution constants (Kd) among combinations of adsorbents and their target ions.
Figure 6A:
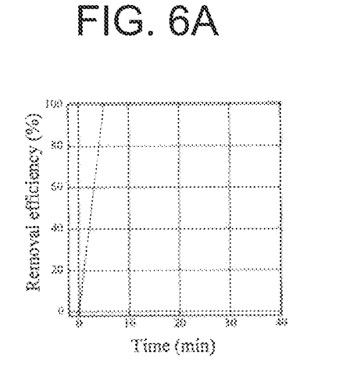
FIGS. 6A and 6B are graphs showing the relationship between $Sr^{2+}$ ion adsorption and $Ba^{2+}$ ion adsorption, respectively, and the reaction time.
Figure 6B:
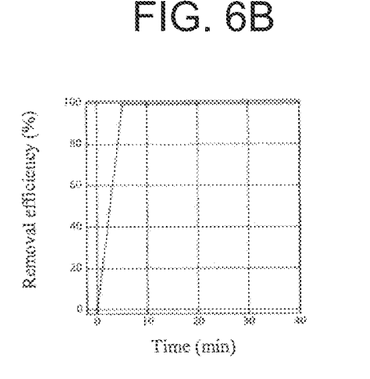

The results of strontium and barium uptake testing will be described referring to FIG. 5 and FIGS. 6 (a) and 6 (b). FIG. 5 is a comparison table of distribution constants (Kd) among combinations of adsorbents and their target ions. FIG. 6 (a) is a graph showing the relationship between $Sr^{2+}$ ion adsorption and the reaction time, and FIG. 6 (b) is a graph showing the relationship between $Ba^{2+}$ ion adsorption and the reaction time.

20 mg of $(NH_4)[Tb(C_2O_4)_2(H_2O)]$ was added to a solution containing 162 ppm of strontium or 200 ppm of barium and stirred at 500 rpm for 10 minutes. The solution was then subjected to filtering, and the concentration of strontium or barium in the solution was measured to obtain the distribution constant (Kd) for strontium or barium. The results showed that the distribution constant for strontium and the distribution constant for barium of $(NH_4)[Tb(C_2O_4)_2(H_2O)]$ were $3.1\times10^4$ and $1.4\times10^5$ (ml/g), respectively. This distribution constant (Kd) for strontium was equivalent to those with zeolites, which are considered to be particularly effective in cleanup of strontium (see FIG. 5). Also, as seen from FIGS. 6 (a) and 6 (b), showing the testing results of adsorption behavior, it was found that this adsorption agent or element separating and recovering agent is capable of removing 99% or more ions in a solution in 10 minutes, which means it is a material that exhibits a much faster adsorption speed than those of zeolites and is capable of efficiently separating specific ions.

The distribution constants (Kd) were obtained by the following formula:

$$K_d(\text{mLg})^{-1}) = \frac{C_i - C_e}{C_e} \times \frac{V}{M} \quad [\text{Formula 4}]$$

wherein Ci represents the initial concentration of the ions in the solution (ppm), Ce represents the concentration of the ions in the solution at equilibrium (ppm), V represents the amount of the solution (2 ml), and M represents the amount of the element separating and recovering agent, $(NH_4)[Tb(C_2O_4)_2(H_2O)]$, as an adsorbent (0.02 g).

Figure 7:
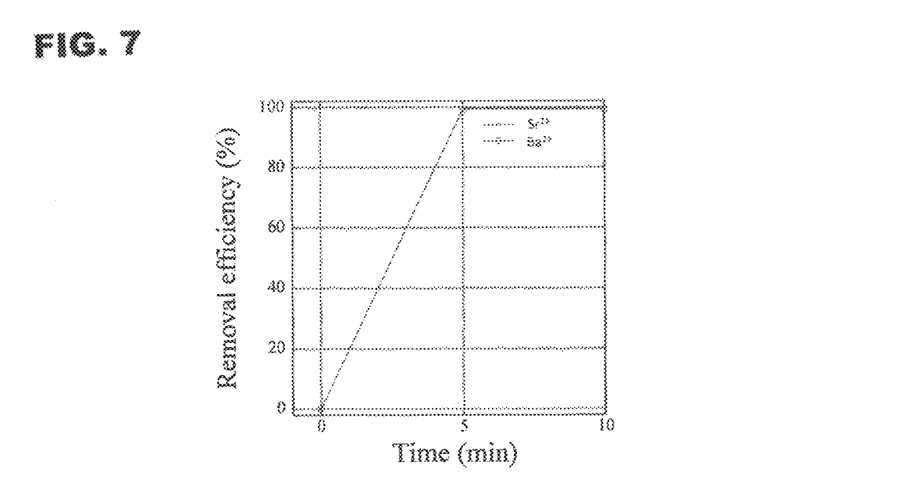
FIG. 7 is a graph showing $Sr^{2+}$ ion adsorption and $Ba^{2+}$ ion adsorption, respectively, from seawater and the reaction time.
Figure 8:
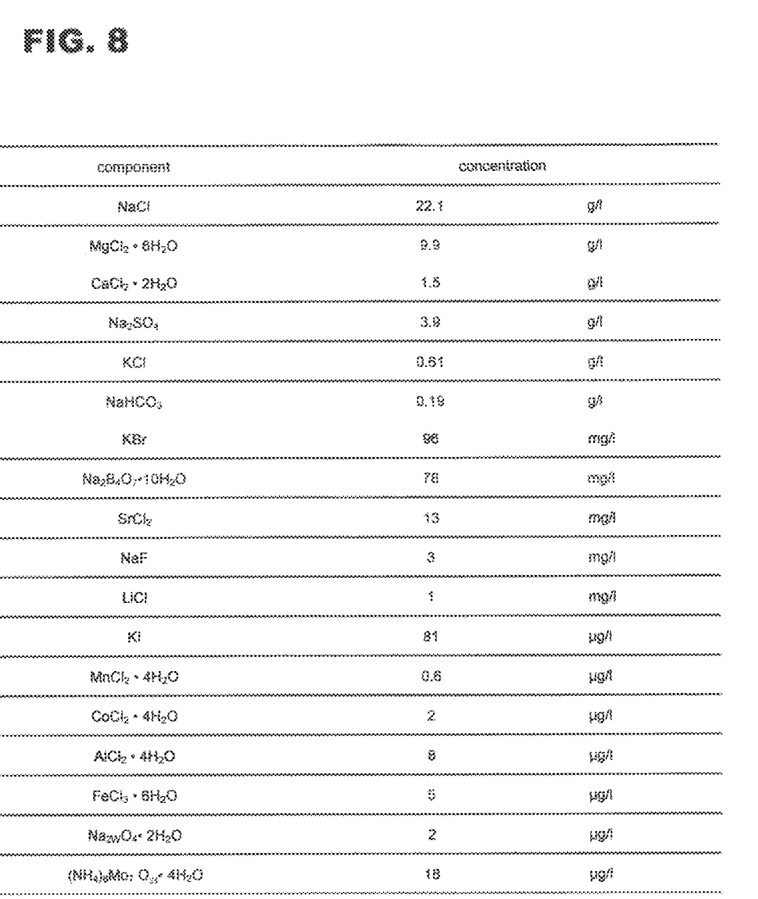
FIG. 8 is a composition table of artificial seawater Marine Art SF-1.

<Experiment 3> Ion Separation from Seawater 20 mg of $(NH_4)[Tb(C_2O_4)_2(H_2O)]$ was added to an artificial seawater Marine Art SF-1 (Osaka Yakken, Osaka, Japan, see the table of FIG. 8) containing 200 ppm of strontium or 200 ppm of barium and stirred at 500 rpm for 10 minutes. The solution was then subjected to filtering, and the concentration of strontium or barium in the solution was measured. The results showed that the distribution constant for strontium and the distribution constant for barium of $(NH_4)[Tb(C_2O_4)_2(H_2O)]$ were $8.2\times10^3$ or higher and $2.5\times10^3$ or higher (ml/g), respectively. Considering the fact that in the efforts to search for adsorbents in Fukushima, distribution constants for strontium in seawater have been reported to be around 1,000 $(ml/g)^{1,2}$, this distribution constant (Kd) for strontium in seawater proved to be much higher than those with adsorbents reported so far. Also, since it was capable of separating target elements from an environment full of other ions like seawater, it was revealed to be a separating agent highly capable of selectively separating elements (see FIGS. 7 (a) and (b)).

Figure 9A:
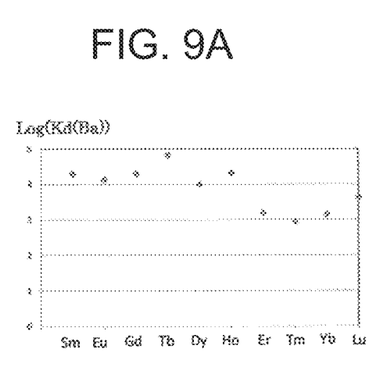
FIGS. 9A and 9B are graphs showing the relationship between the log (Kd) for barium uptake and the log for strontium uptake, respectively, and lanthanide ions.
Figure 9B:
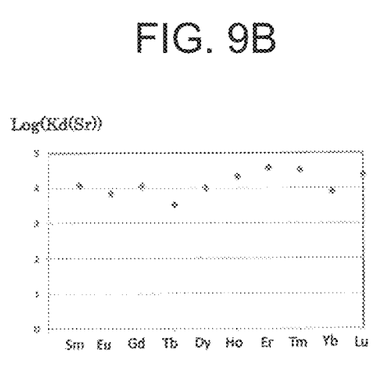

<Experiment 4> Selective Ion Uptake with Different Lanthanide Ions 20 mg of $(NH_4)[Ln(C_2O_4)_2(H_2O)]$ was added to a solution containing 20 ppm of strontium or 20 ppm of barium and stirred at 500 rpm for 10 minutes. The solution was then subjected to filtering, and the concentration of strontium or barium in the solution was measured to obtain the logarithm (log $(K_d)$) of the distribution constant with different metal elements. The results are shown in FIGS. 9A and 9B. As seen from FIGS. 9A and 9B, central metals with a higher log $(K_d)$ exhibit a higher adsorption capability.

Figure 10:
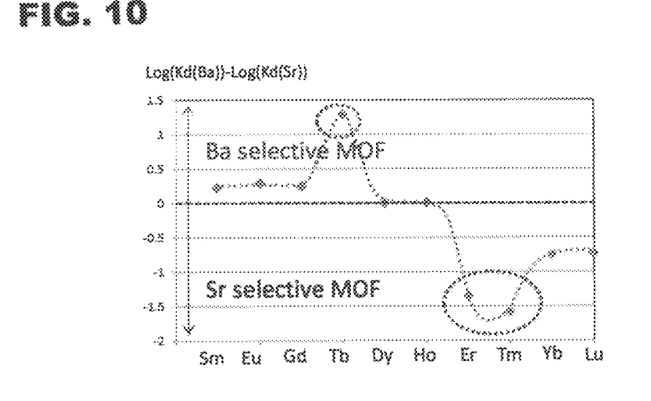
FIG. 10 is a graph showing the relationship between the affinity for barium and strontium and central metals.

For comparison between affinity for barium and affinity for strontium, the difference between the log for Ba, Log (Kd (Ba)), and the log for Strontium, Log (Kd (Sr)), for each metal is shown in FIG. 10. Herein, each log (Kd) is a chemically significant value that indicates a free energy difference when the target element is taken up. FIG. 10 shows that, in general, the larger the pore size is, the higher the affinity for barium is, and the smaller the pore size is, the higher the affinity for strontium is. It also shows that with the lanthanide metals between Tb and Er, there is no difference between barium uptake and strontium uptake. These results indicate that since barium has a larger ionic size than that of strontium[1], barium is taken up by coordination polymers with larger pores more easily than strontium. Also, the affinity for barium is particularly high with the central metal being Tb, and the affinity for strontium is particularly high with the central metal being Er or Tm. Based on these results, it was successfully proved and found that there exists a material that has a pore size that is suited for the ionic radius of each metal.

<Experiment 5> Release of Radioactive Element from Coordination Polymer

Figure 11A:
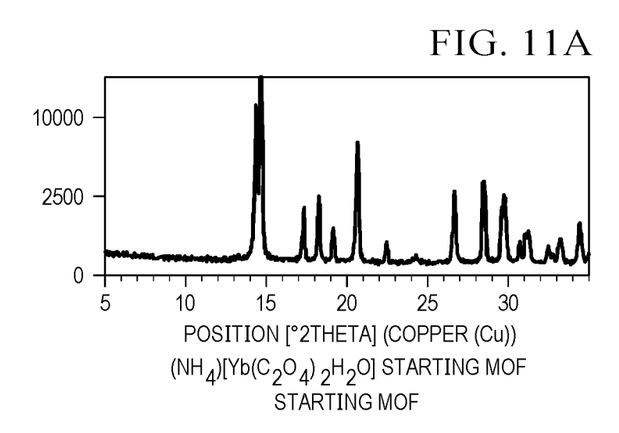
FIGS. 11A to 11D show changes in powder X-ray pattern caused by cesium uptake, cesium release, and a regeneration reaction.
Figure 11B:
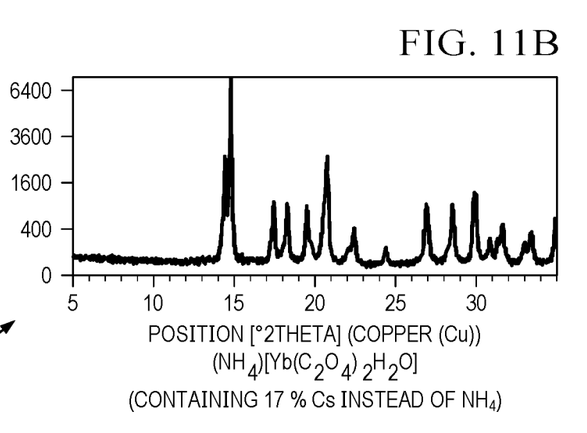

(1) 100 mg of $(NH_4)[Yb(C_2O_4)_2(H_2O)]$ was soaked in 10 ml of a cesium chloride solution (cesium concentration: 1,000 ppm) for four hours (298K, pH 7±1). It was observed that the cesium concentration in the solution had reduced by 61%. In this process, the powder X-ray pattern changed from a) to b) in FIG. 11. Since the change in powder X-ray pattern was small, and the change in chemical structure and state was little, the cesium uptake is considered to have been caused mainly by the reaction expressed by the following formula:

[Formula 5]

Figure 11C:
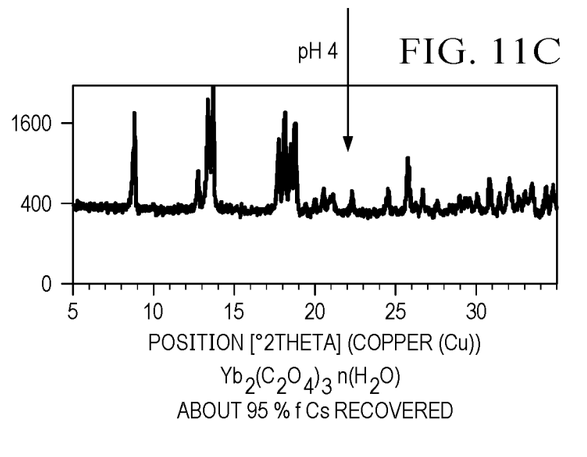

(2) Next, the solution was filtered to obtain the powder, which was then suspended in 10 ml of pure water. To the obtained suspension, 0.001 ml of NHCl was added by an automatic titrator to keep its pH at 4, which allowed release of 95% of the cesium taken up in the polymer into the solvent. In this process, the powder X-ray pattern changed from b) to c) in FIG. 11. Since the powder X-ray pattern is for $Yb_2(C_2O_4)_3 \cdot n(H_2O)$, the cesium release is considered to have been caused by the acidolysis reaction expressed by the following formula:

[Formula 6]

Figure 11D:
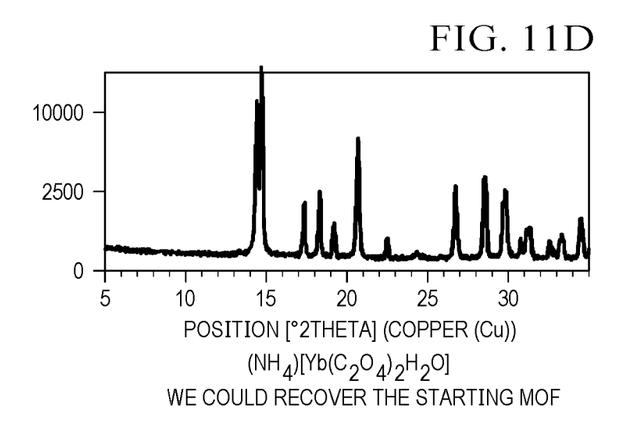

(3) Next, the suspension was filtered to obtain the powder, or $Yb_2(C_2O_4)_3 \cdot n(H_2O)$, to which dimethyl oxalate and ammonium chloride were added, and the mixture was heated at 130° C. for 24 hours. As a result, the powder X-ray pattern changed from c) to d) in FIG. 11. Since the powder X-ray pattern is for $(NH_4)[Yb(C_2O_4)_2(H_2O)]$, the original coordination polymer is considered to have been regenerated by the reaction expressed by the following formula:

[Formula 7]

It was proved that through the reactions as described above, this coordination polymer is capable of taking up cesium, releasing the cesium that it has taken up, and being restored to the original coordination polymer after the release and the use.

What is claimed is:
1. A separation and recovery agent comprising a compound represented by the following molecular formula:
   $(NH_4)[Ln(C_2O_4)_2(H_2O)]$
   wherein Ln represents Tb, and
   wherein the compound is produced by a process consisting of:
   (a) immersing dimethyl oxalate and terbium chloride hexahydrate in an ammonium chloride-containing aqueous solution;
   (b) heating the solution from (a) at 130° C. for 24 hours;
   (c) filtering the solution from (b) to separate crystals;
   (d) cleansing the crystals from (c); and
   (e) drying the crystals from (d),
   wherein the separation and recovery agent is crystalline, and
   wherein single crystal X-ray structure analysis of the separation and recovery agent exhibits a monoclinic crystal system; a P2/n space group; a=9.380(5)(Å); b=6.130(4)(Å); c=7.851(5)(Å); V=451.4(Å³); and Z=2.

* * * * *